United States Patent
Mukherjee et al.

(10) Patent No.: US 7,759,098 B2
(45) Date of Patent: Jul. 20, 2010

(54) PROCESS FOR IMMOBILIZED NANO-SIZED METAL PARTICLES

(75) Inventors: Priyabrata Mukherjee, Maharashtra (IN); Ahmad Absar, Maharashtra (IN); Deendayal Mandal, Maharashtra (IN); Satyajyoti Senapati, Maharashtra (IN); Mohammed Islam Khan, Maharashtra (IN); Murali Sastry, Pune (IN); Rajiv Kumar, Maharashtra (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 12/129,451

(22) Filed: May 29, 2008

(65) Prior Publication Data

US 2008/0227167 A1  Sep. 18, 2008

Related U.S. Application Data

(63) Continuation of application No. 11/157,247, filed on Jun. 20, 2005, now abandoned, which is a continuation of application No. 10/869,548, filed on Jun. 15, 2004, now abandoned, which is a continuation of application No. 10/032,206, filed on Dec. 21, 2001, now abandoned.

(51) Int. Cl.
*C12P 11/00* (2006.01)
*C12P 3/00* (2006.01)
*C12N 1/16* (2006.01)

(52) U.S. Cl. .................... 435/174; 435/168; 435/254.1; 977/703

(58) Field of Classification Search ................ None
See application file for complete search history.

(56) References Cited

U.S. PATENT DOCUMENTS

| 6,225,047 B1 | 5/2001 | Hutchens et al. |
| 6,537,344 B2 | 3/2003 | Mukherjee et al. |
| 7,276,283 B2 | 10/2007 | Denes et al. |

OTHER PUBLICATIONS

Mukherjee et al "Bioreduction of AuCI4- Ions by the Fungus, *Verticillium* sp. and Surface Trapping of the Gold Nanoparticles Formed" Oct 2001 Agnew Chem Int Ed vol. 40 No. 19 pp. 3585-3588.*

Mukherjee et al. "Fungus-Mediated Synthesis of Silver Nanoparticles and their Immobilization in the Mycelial Matrix" Nano Letters 2001 1 (10) pp. 515-519 Publication Web Aug. 30, 2001.*

Dean A. Handley, "Methods for Synthesis of Colloidal Gold", Colloidal Gold: Principles Methods and Applications, Hayat, M.A. Editor, Academic Press, San Diego, CA. 1989, vol. 1, Chapter 2, pp. 13-32 and 1 page of cover.

* cited by examiner

*Primary Examiner*—Herbert J. Lilling
(74) *Attorney, Agent, or Firm*—Merchant & Gould P.C.

(57) ABSTRACT

The present invention provides a new process using biological method for the preparation of immobilized nano-particles of metals. Fungi are used to efficiently prepare immobilized nano-particles of various metals ions such as Au, Ag, Pd, Pt, Ni, Rh and Ru from their aqueous solutions.

16 Claims, No Drawings

PROCESS FOR IMMOBILIZED NANO-SIZED METAL PARTICLES

CROSS REFERENCE TO RELATED APPLICATIONS

This application is a continuation of U.S. patent application Ser. No. 11/157,247, filed on Jun. 20, 2005, which is a continuation of Ser. No. 10/869,548, filed Jun. 15, 2004, which, in turn, is a continuation of Ser. No. 10/032,206, filed Dec. 21, 2001, the disclosures of which are hereby incorporated by reference.

FIELD OF THE INVENTION

The present invention relates to a process for preparing immobilized nano-sized metal particles. More particularly, the present invention relates to a new and improved process employing an efficient, easy and environmentally friendly method for preparing stable, immobilized colloidal nano-particles in aqueous solutions using naturally occurring biomaterials such as fungi.

BACKGROUND OF THE INVENTION

Nano-particles are extremely important materials in different areas ranging from nano-technology, non-linear optics, diode lasers, smart sensors, markers in drugs, gene sequencing to catalysis. Nano-materials can be obtained by various chemical and physical methods. Some examples of physical methods are vapour deposition, lithographic processes and molecular beam epitaxy (MBE). Chemical methods include the popular borohydride and citrate reduction methods for the preparation of colloidal metal (like gold, silver etc.) particles. Reference may be made to D. A. Handley, *Colloidal Gold: Principles, Methods and Applications*; Hayat, M. A. Editor, Academic Press, San Diego, Calif. 1989; Vol. 1, Chapter 2, wherein details of such chemical routes are given. Reduction of metal ions by radiolysis is also conventionally used for preparing nano-sized metal particles. However, the methods mentioned above suffer from drawbacks such as being environmentally hazardous (chemical methods) and result in the quick agglomeration of nano-particles leading to big particles for poor monodispersity.

Although specific capping agents are used in some of the abovementioned methods to restrict the size of the colloidal metal particles and to stabilize the particle size distribution, this makes the whole system quite complicated and user unfriendly. Another disadvantage, particularly of the radiolysis method, is that it is quite complicated and gamma ray sources are not readily available.

OBJECTS OF THE INVENTION

The main object of the invention is to provide an improved process for preparing immobilized nano-sized metal particles using an environment friendly biological method.

Another object of the invention is to provide a process which uses naturally occurring fungi under aqueous medium.

Another object of the invention is to provide the process for preparation of nano-sized metal particles, which are deposited on to the fungus cell wall.

Another object of the invention is to provide a process where the formation of nano-particles occurs on the surface of biomass and not in the solution.

SUMMARY OF THE INVENTION

Accordingly the present invention provides an improved process for preparing immobilized nano-sized metal particles, which comprises treating wet fungal mycelia with a metal ion solution at temperature in the range of 15 to 40° C. for a period in the range of 2 to 120 hours, separating the biomass to obtain the immobilized nano-sized metal particles deposited on to the surface of the fungal cells.

In an embodiment of the present invention the wet fungal mycelia is obtained by growing the *Verticillium* (AAT-TS-4) in a culture medium for a period of 2 to 120 hours at temperature ranging between 15-40° C. under aseptic conditions, separating the biomass by centrifugation, washing several times with sterile water, and then incubating the whole reaction mixture at 15 to 40° C. and atmospheric pressure.

In another embodiment the metal ion solution is obtained by dissolving metal salts of group IB-VIIIB metals in water.

In a further embodiment of the invention, the metal is selected from the group consisting of Au, Ag, Pd, Pt, Ni Rh and Ru.

In a further embodiment of the invention, the metal salts are selected from the group consisting of halides, nitrates and carbonates.

In another embodiment the metal ion solution is obtained by dissolving the acidic form of metals in water.

In a further embodiment of the invention, the acidic form of the metal is selected from chloroauric acid and chloroplatinic acid.

In another embodiment of the invention concentration of metal ions per gram of wet fungal mycelia is in the range of 10 to 200 mg metal ions per gram of wet fungal mycelia.

In another embodiment of the invention concentration of metal ions per gram of wet fungal mycelia is in the range of 10 to 100 mg metal ions per gram of wet fungal mycelia.

In another embodiment of the invention concentration of metal ions per gram of wet fungal mycelia is in the range of 25 to 100 mg metal ions per gram of wet fungal mycelia.

In yet another embodiment of the invention ratio of water to wet fungal mycelia is 100:1 (w/w) In another embodiment of the invention the fungus *Verticillium* designated as AAT-TS-4 is taken as whole cell as wet solid mass.

In another embodiment of the invention, reaction of the fungus and a source of metal ions in solution is carried out in water.

In another embodiment of the invention the incubation/reaction temperature is in the range of 15-40° C., preferably 23-33° C., most preferably 25-29° C.

The process for the present invention is described herein below with examples that are illustrative and should not be construed to limit the scope of the present invention.

EXAMPLE 1

In this experiment, 10 g of wet fungal mycelia (*Verticillium* AAT-TS-4), grown in a culture medium, separated from medium by centrifugation, washed several times with water through centrifugation, was taken in a autoclaved conical flask and then 100 ml solution of 100 mg of $HAuCl_4$ in water was added.

The conical flask was then plugged with cotton and incubated at 27° C. Samples were collected periodically by filtration of solution containing the fungus inside the inoculation chamber under laminar flow condition. Bio-transformation was routinely monitored by visual inspection of the biomass as well as measurement of UV-vis spectra from the fungal cells.

Films of the fungal cells (both before and after exposure to Au$^+$ ions for 72 h) for UV-vis spectroscopy and scanning electron microscopy (SEM) studies were prepared by solution casting fungal cells onto Si (111) wafers and thoroughly drying film in flowing N$_2$. UV-vis spectroscopy measurement of films were made on a Shimadzu dual-beam spectrophotometer (model Uv-1601PC) operating the reflection mode at a resolution of 2 nm.

These data confirm the presence of gold nano-particles on to the surface of the biomaterial. UV-vis spectra of the clear aqueous solution after reaction with the mycelial cells for 72 h showed the absence of the characteristic plasmon resonance band of gold ca 433 nm indicating the absence of gold in the solution.

EXAMPLE 2

In this experiment, 10 g of wet fungal mycelia (*Verticillium*), grown in a culture medium, separated from medium by centrifugation, washed several times with water through centrifugation, was taken in an autoclaved conical flask and then a solution containing 25 mg of HAuCl$_4$ in 100 ml water was added.

The conical flask was then plugged with cotton and incubated at 27° C. Samples were collected periodically by filtration of solution containing the fungus inside the inoculation chamber under laminar flow condition. Bio-transformation was routinely monitored by visual inspection of the biomass as well as measurement of the UV-vis spectra from the fungal cells.

Films of the fungal cells (both before and after exposure to Au$^+$ ions for 72 h) for UV-vis spectroscopy and scanning electron microscopy (SEM) studies were prepared by solution casting the fungal cells onto Si (111) wafers and thoroughly drying the film in flowing N$_2$. UV-vis spectroscopy measurements of the films were made on a Shimadzu dual-beam spectrophotometer (model UV-1601PC) operating in reflection mode at a resolution of 2 nm.

These data confirm the presence of gold nanoparticles on the surface of the biomaterial. UV-vis spectra of the clear aqueous solution after reaction with the mycelial cells for 72 h showed the absence of the characteristic plasmon resonance band of gold ca 533 nm indicating the absence of gold in the solution.

EXAMPLE 3

In this experiment, 10 g of wet fungal mycelia (*Verticillium*), grown in a culture medium, separated from medium by centrifugation, washed several times with water through centrifugation, was taken in an autoclaved conical flask and then 250 mg of HAuCl$_4$ in 100 ml water was added.

The conical flask was then plugged with cotton and incubated at 27° C. Samples were collected periodically by filtration of solution containing the fungus inside the inoculation chamber under laminar flow condition. Bio-transformation was routinely monitored by visual inspection of the biomass as well as measurement of the UV-vis spectra form the fungal cells.

Films of fungal cells (both before and after exposure to Au$^+$ ions for 72 h) for UV-vis spectroscopy and scanning electron microscopy (SEM) studies were prepared by solution casting fungal cells onto Si(111) wafers and thoroughly drying the film in flowing N$_2$. UV-vis spectroscopy measurements of the films were made on a Shimadzu dual-beam spectrophotometer (model WV-1601IPC) operating in reflection mode at a resolution of 2 nm.

These data confirm the presence of gold nano-particles on the surface of the biomaterial. UV-vis spectra of the clear aqueous solutions after reaction with the mycelial cells for 72 h showed the absence of the characteristic plasmon resonance band of gold ca 533 nm indicating the absence of gold in the solution.

EXAMPLE 4

In this experiment, 10 g of wet fungus (*Verticillium*) grown in a culture medium, separated from medium by centrifugation, washed several times with water through centrifugation, was taken in an autoclaved conical flask and then 125 mg AgNO$_3$ in 100 water was added.

The conical flask was then plugged with cotton and incubated at 27° C. Samples were collected periodically by filtration of solution containing the fungus inside the inoculation chamber under laminar flow condition. Presence of nano sized Ag particles deposited on to the fungal cells was confirmed by evolution of plasmon resonance band around 400 nm. The brown coloration is a clear indication of formation of silver nano-clusters. The range of the silver nano-particles size was found to be 5-80 nm.

EXAMPLE 5

In this experiment, 10 g of wet fungal mycelia (*Verticillium*), grown in a culture medium, separated from medium by centrifugation, washed several times with water through centrifugation, was taken in a autoclaved conical flask and then 50 mg AgNO$_3$ in 100 ml water was added.

The conical flask was then plugged with cotton and incubated at 37° C. Samples were collected periodically by filtration of solution containing the fungus inside the inoculation chamber under laminar flow condition. Samples were collected between 1 and 86$^{th}$ and each sample was characterized by UV-vis spectroscopy fluorescence spectroscopy, TEM analysis. Evolution of plasmon resonance band around 400 nm and the brown coloration is a clear indication of formation of silver nanoclusters. The range of the silver nanoparticles size was found to be ca. 50 nm.

EXAMPLE 6

In this experiment, 10 g of wet fungal mycelia (*Verticillium*) grown, in a culture medium, separated from medium by centrifugation, washed several times with water through centrifugation, was taken in an autoclaved conical flask and then 100 ml solution containing 100 mg Ni(NO$_3$)$_2$ (nickel nitrate) was added. The conical flask was then plugged with cotton and incubated at 22° C. Samples were collected periodically by filtration of solution containing the fungus inside the inoculation chamber under lamiar flow condition Samples were collected at 86 h and characterized by UV-vis spectroscopy, TEM analysis and by fluorescence spectroscopy. Evolution of plasmon resonance band around 415 nm is clear indication of formation of Ni-nano-clusters in solution. Sizes of the nano-clusters were determined by TEM analysis and found to be 100 nm.

EXAMPLE 7

In this experiment, 10 g of wet fungal mycelia (*Verticillium*) grown in a culture medium, separated from medium by centrifugation, washed several times with water through centrifuigation, was taken in an autoclaved conical flask and then 25 mg NiSO$_4$ in 100 ml water was added.

The conical flask was then plugged with cotton and incubated at 25° C. Samples were collected periodically by filtration of solution containing the fungus inside the inoculation chamber under laminar flow condition. The samples were collected between 1 and 96 h and each stage was characterized by UV-vis spectroscopy fluorescence spectroscopy, TEM analysis. The brown coloration of the fungal mycelial biomass, evolution of the plasmon resonance band around 415 nm and TEM analysis indicated the formation of nickel nanoclusters, deposited on to the fungal cell, in the range of 50-100 nm. No evidence of the presence of Ni in the solution was observed.

EXAMPLE 8

In this experiment, 10 g of wet fungal mycelia (*Verticillium*), grown in a culture medium, separated from medium by centrifugation, washed severed times with water through centrifugation, was taken in an autoclaved conical flask and then 100 ml aqueous solution containing 125 mg of H$_2$PtCl$_6$ (chloroplatinic acid) in water were added.

The conical flask was then plugged with cotton and incubated at 33° C. Samples were collected periodically by filtration of solution containing the fungus inside the inoculation chamber under laminar flow condition. Samples were collected between 1 and 96 h and the sample were characterized by UV-vis spectroscopy, fluorescence spectroscopy, TEM analysis. The evolution of the plasmon resonance band at 215 nm is a clear indication of the formation of Pt-nano-particles deposited on to fungal cell. The samples were further characterized by TEM analysis and the particle size was found to be in the range of 30-50 nm. No evidence could be obtained for the presence of Pt. in solution after the reaction.

It is therefore clear that the present invention provides a new process using biological method for the preparation of immobilized nano particles of metals obviating the drawbacks of the prior art methods. The process of the present invention describes a new biological method, instead of chemical or physical methods for preparing immobilized metal particles. This is the first time that fungi are used to efficiently prepare immobilized nano-particles of various metals ions from their aqueous solutions.

Justification and Advantages of the Present Invention

The use of naturally occurring fungi under aqueous medium.

The immobilized nano-sized metal particles are stable.

The method of the invention is simple and environmentally friendly.

The formation of nano-particles occurs on the surface, therefore immobilizing them and the metal nano-particles are not released in to the solution.

A single step method for obtaining immobilized nano-particles of metals.

The invention claimed is:

1. A process for preparing immobilized nano-sized metal particles comprising treating wet fungal mycelia of *Verticillium* (AAT-TS-4) with a metal ion solution at temperature in the range of 15 to 40° C. for a period in the range of 2 to 120 hours, separating the biomass to obtain the immobilized nano-sized metal particles deposited on to the surface of the fungal cells.

2. A process as claimed in claim 1 wherein the wet fungal mycelia is obtained by growing the *Verticillium* (AAT-TS-4) in a culture medium for a period of 2 to 120 hours at temperature ranging between 15-40° C. under aseptic conditions, separating the biomass by centrifugation, washing several times with sterile water, and then incubating the whole reaction mixture at 15 to 40° C. and atmospheric pressure.

3. A process as claimed in claim 1 wherein the metal ion solution is obtained by dissolving metal salts of group IB-VIIIB metals in water.

4. A process as claimed in claim 3 wherein the metal is selected from the group consisting of Au, Ag, Pd, Pt, Ni, Rh and Ru.

5. A process as claimed in claim 3 wherein the metal salts are selected from the group consisting of halides, nitrates and carbonates.

6. A process as claimed in claim 1 wherein the metal ion solution is obtained by dissolving the acidic form of metals in water.

7. A process as claimed in claim 6 wherein the acidic form of the metal is selected from chloroauric acid and chloroplatinic acid.

8. A process as claimed in claim 1 wherein the concentration of metal ions per gram of wet fungal mycelia is in the range of 10 to 200 mg metal ions per gram of wet fungal mycelia.

9. A process as claimed in claim 8 wherein the concentration of metal ions per gram of wet fungal mycelia is in the range of 10 to 100 mg metal ions per gram of wet fungal mycelia.

10. A process as claimed in claim 8 wherein the concentration of metal ions per gram of wet fungal mycelia is in the range of 25 to 100 mg metal ions per gram of wet fungal mycelia.

11. A process as claimed in claim 1 wherein the ratio of water to wet fungal mycelia is 100:1 (w/w).

12. A process as claimed in claim 1 wherein the fungus *Verticillium* AAT-TS-4 is taken as whole cell as wet solid mass.

13. A process as claimed in claim 1 wherein the reaction of the fungus and metal ion source in solution is carried out in water.

14. A process as claimed in claim 1 wherein the incubation/reaction temperature is in the range of 15-40° C.

15. A process as claimed in claim 14 wherein the incubation/reaction temperature is in the range of 23-33° C.

16. A process as claimed in claim 14 wherein the incubation/reaction temperature is in the range of 25-29° C.

* * * * *